(12) United States Patent
Means

(10) Patent No.: US 6,790,256 B2
(45) Date of Patent: Sep. 14, 2004

(54) GAS CARRY-UNDER MONITORING AND CONTROL SYSTEM

(75) Inventor: C. Mitch Means, Richmond, TX (US)

(73) Assignee: Baker Hughes Incorporated, Houston, TX (US)

( * ) Notice: Subject to any disclaimer, the term of this patent is extended or adjusted under 35 U.S.C. 154(b) by 10 days.

(21) Appl. No.: 10/254,259

(22) Filed: Sep. 25, 2002

(65) Prior Publication Data

US 2003/0051602 A1 Mar. 20, 2003

Related U.S. Application Data

(63) Continuation-in-part of application No. 09/699,018, filed on Oct. 27, 2000, now Pat. No. 6,461,414.
(60) Provisional application No. 60/162,542, filed on Oct. 29, 1999.

(51) Int. Cl.[7] .............................................. B01D 19/00
(52) U.S. Cl. ................... 95/1; 95/155; 95/242; 73/60.11; 96/156; 96/176
(58) Field of Search ..................... 73/60.11, 64.44, 73/61.41; 95/1, 8, 155, 241, 242; 96/417, 456, 136, 181

(56) References Cited

U.S. PATENT DOCUMENTS

| | | | |
|---|---|---|---|
| 1,921,725 A | 8/1933 | Boutet | 183/2.6 |
| 3,739,795 A | 6/1973 | Hyde et al. | 137/5 |
| 4,018,089 A | 4/1977 | Dzula et al. | 73/422 R |
| 4,395,902 A * | 8/1983 | Espenscheid et al. | 73/19.11 |
| 4,426,879 A | 1/1984 | Humphries et al. | 73/60.1 |
| 4,444,044 A | 4/1984 | Humphries et al. | 73/60.1 |
| 4,596,586 A | 6/1986 | Davies et al. | 55/52 |
| 4,624,745 A | 11/1986 | Sande et al. | 162/252 |
| 4,852,395 A * | 8/1989 | Kolpak | 73/61.44 |
| 5,437,842 A | 8/1995 | Jensen et al. | 422/106 |
| 5,547,022 A | 8/1996 | Juprasert et al. | 166/263.5 |
| 5,593,890 A | 1/1997 | Flores-Cotera et al. | 435/286.5 |
| 5,853,617 A | 12/1998 | Gallagher et al. | 252/321 |
| 5,868,589 A | 2/1999 | Swenson, Sr. | 134/18 |
| 5,922,112 A | 7/1999 | Zappi et al. | 435/286.5 |
| 6,461,414 B1 * | 10/2002 | Kohl et al. | 96/156 |
| 2003/0051602 A1 * | 3/2003 | Means | 95/23 |

FOREIGN PATENT DOCUMENTS

EP 0859235 A1 8/1998

* cited by examiner

Primary Examiner—Duane S. Smith
(74) Attorney, Agent, or Firm—Madan, Mossman & Sriram, P.C.

(57) ABSTRACT

A system for monitoring gas carry-under of a formation fluid exiting a gas separator by measuring a parameter of interest of the formation fluid exiting the gas separator is disclosed. The parameter of interest that can be correlated with the extent of gas entrained in the formation fluid exiting the separator can be the density of the formation fluid, or an absorbance spectrum of the formation fluid. A correlation of the measurement of the parameter of interest with a level of gas carry-under is made and a signal is transmitted to a device to control the supply of at least one additive to control the gas carry-under.

13 Claims, 1 Drawing Sheet

GAS CARRY-UNDER MONITORING AND CONTROL SYSTEM

CROSS-REFERENCE TO RELATED APPLICATIONS

This application is a continuation-in-part of U.S. patent application Ser. No. 09/699,018 filed Oct. 27, 2000, now U.S. Pat. No. 6,461,414; which claims priority from U.S. Provisional Patent Application No. 60/162,542 filed Oct. 29, 1999, each assigned to the assignee of this application.

BACKGROUND OF THE INVENTION

1. Field of the Invention

This invention relates generally to oil producing operations, and more particularly to a system and a method for monitoring and controlling foam or hydrocarbon carry-under at a wellsite.

2. Background of the Invention

Oil, also referred to herein interchangeably as crude oil, condensate, or formation fluid, in essentially all reservoirs contains at least some dissolved gases, which exist naturally in the formation. When oil flows upward from the formation through the wellbore(s) to the wellhead, there is a substantial decrease in the pressure because the platform equipment is set up to reduce the high reservoir pressure to a pressure that can be handled by a pipeline system or other downstream equipment. As a result of this drop in system pressure, some of the dissolved gases tend to evolve and become physically separated from the oil to form gas bubbles, i.e. foams.

Although the amount of gases originally dissolved in the formation fluid may not be very large, the effect of lower pressure on their separation can be quite substantial. This is because the same weight of a gas occupies a much larger volume than the corresponding liquid. Depending on the molecular weight, temperature and other conditions, it is not unusual for a small amount of liquid to transform into gas with 100 times or even higher volume. Examples of commonly encountered and naturally occurring gases in formation fluid include, but are not limited to, methane, ethane, carbon dioxide and mixtures.

There is typically a train of several liquid and gas separators installed at a wellsite to separate gases from the formation fluid before it is transported for further processing. The formation fluid itself is may actually be a multiphase liquid having gas and both an aqueous phase and a hydrocarbon phase, commonly referred to as crude oil. In an ideal situation, the evolved gases and formation fluid should separate relatively fast because they are in separate phases and the gas phase bubbles should break out of the fluid phase readily. For a number of reasons, however, the formation fluid-gas separation and even the crude oil-gas separation in practice is usually difficult and incomplete. The main reason is that the gas bubbles in the oil (also referred to as emulsions or foams) are too stable to be effectively broken up at a high oil production rate even with several gas-oil separators because the residence time of the liquid in each separator is kept relatively short. In view of the fact that the industry trend is to have even higher production rate from a producing well, i.e even shorter residence times in the separators, and drilling into formations in deeper water, the problem with foaming may become even more severe. While it is certainly possible to build and use larger gas-oil separators, this option may not be desirable or practical because such separators would require much higher capital investments and more space on oilfield platforms.

Foaming is undesirable because it is usually an unpredictable and metastable phenomenon, which may interfere with the gas-oil separation efficiency or the operations of the oil well(s); the resultant carryover of liquid in the form of either foam or mist/droplets of oil entrained in the gas stream exiting the gas-oil separators will enter into downstream equipment or pipeline. Too much of such liquid carryover can cause severe operating problems, such as flooding for the downstream gas transportation equipment, pipeline or gas processing plants.

Similarly, entrainment of gas in the liquid stream from the separators, hereinafter referred to as gas carry-under, can be very undesirable as well. The gases entrained in the liquid stream can cause both processing and safety problems. For example, such gas can cause over pressuring of vessels downstream from the separators. The gas can be in the form of entrained gas bubbles or it can be in the form of dissolved gasses. In either case, the result of such entrained gas can be its unexpected evolution at a point in the process where it can not be well handled from a safety perspective, environmental perspective, an operating perspective, or a combination of one or more of these. In addition to this, where the main objective is the production of crude oil, incorporation of gas into the crude oil decreases the efficiency with which the crude oil can be transported because the gas is taking up space (volume) thereby decreasing the volume of crude oil being transported. Where the primary objective is the production of natural gas, the loss of gas into the crude oil or aqueous streams exiting a separator is undesirable.

One reason for the existence of stable foam, thus the foaming and gas carry-under problem, is that many surfactants exist naturally in or near the producing formations. Such surfactants, with their ability to stabilize emulsions or foams, cause the foaming and gas carry-under problem to become more pronounced and longer lasting, particularly when the formation fluid reaches the production facilities at the wellhead on the surface as noted above. Moreover, many chemicals or additives are injected into oil wells by the operator to provide functions such as corrosion inhibition, asphaltenes suppression, etc. and may also act as surfactants under the producing conditions to further stabilize the emulsions, thus exacerbating the foaming and gas carry-under problem.

Another factor affecting gas carry-under occurs when the formation fluid flows from the producing formation toward the wellbores of the producing wells. The flow rate near the wellbores becomes higher than that in other parts of the reservoir. This higher flow rate tends to cause the formation fluid to trap and mix with any water that may be in the vicinity of the wellbore, or any steam that is injected into the wellbore by the operator. In the presence of either natural or injected chemicals behaving as a surfactant, this type of oil-water emulsion also can further intensify the gas carry-under problem at or down stream from the wellhead.

In typical land or offshore oil production wells, the formation fluid from the wellbores flows through a wellhead choke into a high-pressure manifold, which is used if there are multiple wells at a particular site. The fluid then passes through one or more heat exchangers to recover useable heat into a high-pressure (HP) gas-oil separator. There are usually several separators—a train of separators—for one oil-processing platform. The primary functions of these separators are to separate the gas and liquid components of the oil and to reduce the pressure in a stepwise manner. Such a train of separators commonly comprises a HP separator, an intermediate pressure (IP) separator, a low-pressure (LP) separator, and a test separator, with the HP separator being closest to the wellhead choke and having the largest pressure drop. In order to conserve energy by not having to repressurize, it is preferred to separate gas from oil at as high a pressure as possible.

The gas phase of the production fluid rapidly expands downstream of the wellhead choke, and continues to expand further downstream through pressure control valves as the fluid travels through the train of gas-oil separators. Any natural surfactants or other additives injected into the well that can act as surfactants tend to create a gas carry-under problem.

It is therefore desirable to have a reliable system to determine the extent of gas carry-under of the formation fluid recovered through a wellbore at the wellsite. It is also desirable to use the obtained gas carry-under information to control gas carry-under at the wellsite. The present invention addresses the above-noted needs and provides a wellsite foam monitoring and controlling system that (a) determines the extent of foam carry-under, (b) determines the extent of the treatment required to alleviate the gas carry-under problem, and (c) controls the dispensing of additives to inhibit or alleviate the gas carry-under problem.

SUMMARY OF THE INVENTION

The present invention provides a system for determining and controlling, particularly at a wellsite, the gas carry-under of a formation fluid passing through at least one liquid and gas separator that provides a gas stream separated from the formation fluid. The system comprises a sensor for providing measurements of a parameter of interest relating to the liquid stream passing from the separator that is indicative of gas carry-under occurring in the formation fluid, and a processor utilizing the sensor measurements for determining degree of gas carry-under of the formation fluid.

In a preferred embodiment of the present invention, the sensor is a particle-detecting sensor based on light scatter or transmission. In another embodiment, the sensor is a attenuated total reflectance (ATR) probe. In either embodiment, the sensor is placed directly in the exit stream from a separator.

In another aspect of the invention, there is a chemical injection unit for supplying a chemical to the formation fluid for optionally controlling gas carry-under occurring in the formation fluid. The chemical injection unit injects the chemical at one or more of the following location; (i) in one or more of the liquid gas separators; (ii) in a well producing the formation fluid; (iii) a wellhead at the surface; (iv) a selected number of wells from a plurality of wells providing formation fluid to the separator(s). The chemical injection is increased when the degree of gas carry-under is outside a predefined limit.

BRIEF DESCRIPTION OF THE DRAWINGS

For a detailed understanding of the present invention, reference should be made to the following detailed description of the preferred embodiments, taken in conjunction with the accompanying drawings, in which like elements have been given like numerals, wherein.

DETAILED DESCRIPTION OF THE PREFERRED EMBODIMENTS

This invention relates to a system and method for monitoring and controlling gas carry-under, preferably at a wellsite. The monitoring is carried out by monitoring a liquid stream to determine the amount of carried-over gas in the liquid stream exiting a separator device. In one embodiment, a density measurement is performed. The measured density is correlated with the amount of gas in the exiting liquid stream. This amount is a function of and proportional to the degree of gas carry-under in the particular separator or other equipment. The system may further include a chemical injection unit that alters the amount of chemicals injected into the formation fluid to reduce or eliminate gas carry-under in the formation fluid.

Figure 1:
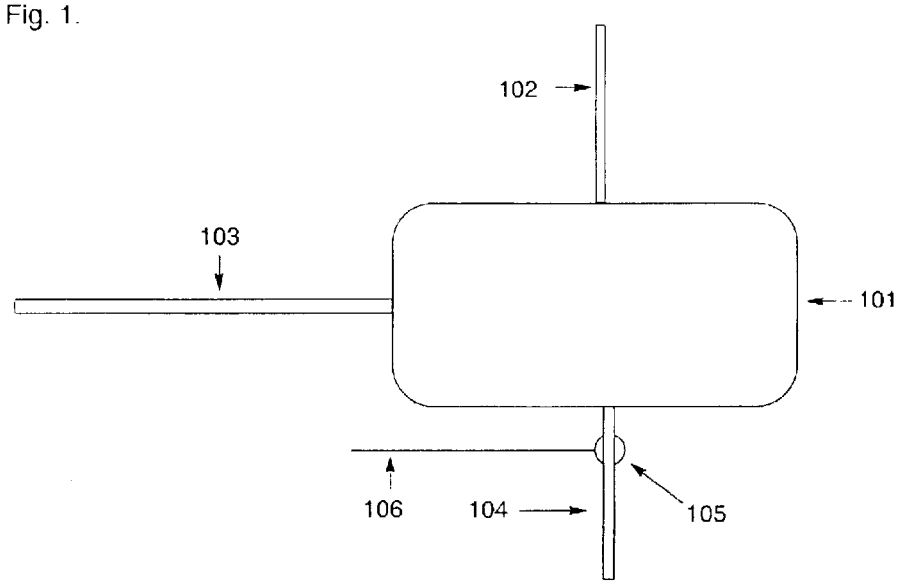
FIG. 1 illustrates a gas carry-under monitoring system according to one embodiment of the present invention, wherein a sensor is used to measure a parameter, of a liquid stream exiting an HP oil-gas separator, the paramenter being indicative of gas carry-under.

Illustrations of examples of the preferred systems and methods of the present invention are provided below. FIG. 1 illustrates a gas carry-under monitoring system according to one embodiment of the present invention, wherein a sensor is used to measure a parameter, of a liquid stream exiting an HP oil-gas separator, the parameter being indicative of gas carry-under. The system includes a high-pressure liquid gas separator 101 that receives formation fluid from the wellhead via line 103. The separator 101 separates oil, water and any other liquids from vaporous gas that gas exits via a pipe 102 to a gas outlet (not shown) that is connected to other separators such as an IP separator (also not shown).

A sensor 105 provides a measurement of a parameter that can be correlated with gas carry-under in the formation fluid leaving the separator 101 by means of an exit pipe 104. For example, a densitometer can be used as the sensor 105 and a measurement of the density of the formation fluid is made. The densitometer 105 provides measurements or a signal, which can be correlated to the density of the fluid in the exit pipe 104. The signal is carried from the sensor 105 by means of a data line 106.

Figure 2:
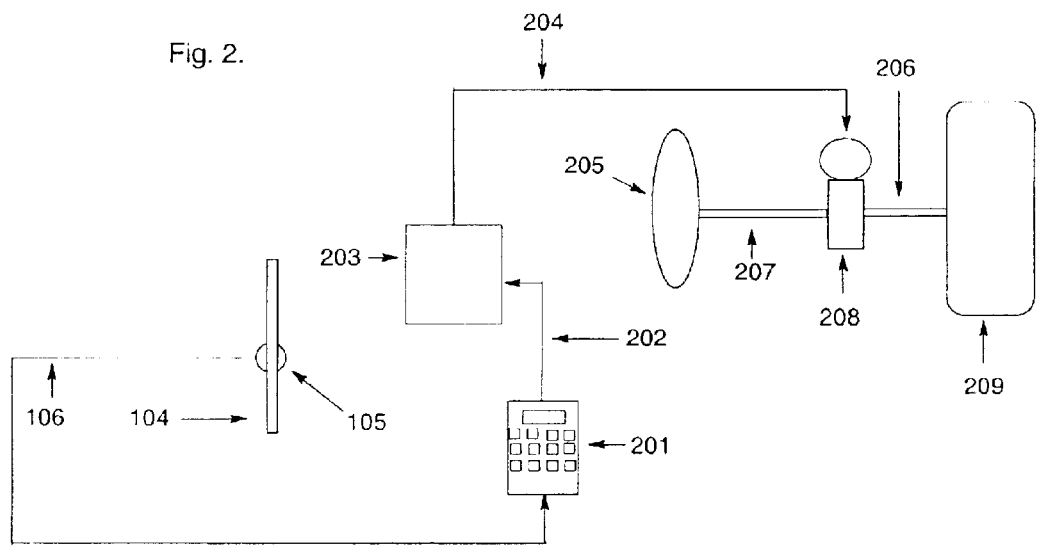
FIG. 2 is a schematic illustration of a chemical injection system for controlling chemical injection in response to gas carry-under measurements in liquid exiting the separator shown in FIG. 1, according to one embodiment of the present invention.

FIG. 2 is a schematic illustration of a chemical injection system for controlling chemical injection in response to gas carry-under measurements in liquid exiting the separator shown in FIG. 1, according to one embodiment of the present invention. In one embodiment, the gas carry-under monitoring system includes a wellsite display 201 and a processor 203 that may include some or all of the necessary computer programs and software to perform the necessary calculations, correlations, comparisons to make a determination of the extent of gas carry-under in the formation fluid exiting the separator 101. Data/signals from the sensor 105 are passed to the display 201, which displays the density and/or flow rate and/or gas content of liquid stream, by means of the data line 106. The data/signals are then further passed to a processor 203 by means of a second data line 202. The connection may be wired or the data lines can represent a wireless transmission or even a local area network. The processor 203 may be programmed to transmit data to a controller 208 located locally, at the wellsite, or at another suitable remote location via a data transfer line or remote link 204.

One embodiment of the present invention is a gas carry-under control system. The local display 201 and processor 203 is connected to a controller 208, which may be a second processor with the necessary computer programs and software to perform all or part of the necessary calculations, correlations, comparisons to make a determination of gas carry-under, or it may be a simple pump controller which only functions to control the rate at which an additive is supplied into the formation fluid.

The controller 208 adjusts the rate at which an additive or additive mixture from an additive storage tank 209 (source) is supplied through a flow line (206 and 207) to a suitable injection location 205. The portions of this system that respond to the signal from the sensor 105 to adjust the rate of flow of the additive to control gas carry-under can be specially prepared to perform only this function or it can be a commercially available system, such as the SENTRY-NET™ additive control system available from Baker Petrolite. The system can be manual, partially automated, and particularly in the case where a SENTRYNET additive control system is incorporated into the system of the present invention, the system can be fully automated. The other pumps and the associated flow controllers are not shown in FIG. 2.

As noted above, the gas carry-under level is determined in this invention by determining and quantifying the amount of gas entrained in the liquid exiting a separator by a processor or controller at or near the separator site or at a remote location. The processor then causes a chemical injection unit to control or adjust the type and/or amount of additives injected into the separator(s) and/or the well. This provides a closed loop system, which minimizes the use of additives and chemicals for controlling gas carry-under.

The amount of gas in the liquid may be determined by a number of methods. For instance, a batch sample can be collected over a period of time and then analyzed in a laboratory. This is an indirect method, not preferred for the practice of the present invention directly, but useful in calibrating the sensor of the present invention. An example of a direct method uses a suitable densitometer to measure the density of the liquid and the density data can be correlated with the amount of gas present in a liquid stream, preferably using lab data to calibrate the densitometer. The amount of gas can be correlated with gas carry-under.

It is also a preferred embodiment of the present invention to use an optical probe as the sensor of the present invention. It is preferred to use a fiber optic probe, and particularly preferred to use an attenuated total reflectance probe, with a photometer to directly measure the amounts of gas occurring in a formation fluid. By measuring the absorbance in a wavelength range of 400 nm to 1500 nm and then transmitting the results to a data gathering and processing circuit or unit such as a microprocessor based unit or a computer for data analysis, the amount of gas entrained in the formation fluid exiting a separator can be determined.

Photometers useful with the present invention include single wavelength photometers, spectrophotometers, UV-VIS-NIR spectrophotometers, and the like. For the purposes of the present invention, the term ATR means an attenuated total reflectance device including a probe and a means of measuring the refractance of a material in contact with the probe.

An ATR is a preferred optical probe for the practice of the present invention because it is readily available and permits both in-laboratory measurements and real-time direct measurements of the absorbance of highly opaque or colored fluid or liquid within a process. Formation fluids, such as crude oil, are normally opaque and dark. It is necessary that the probe be capable of withstanding contact with formation fluid at the conditions in or at least near a separtor. For example, ATR probes having sapphire windows are particularly preferred for use with the present invention.

The readings of the absorbance spectra of a typical formation fluid, such as a well stream, are made at a wavelength ranging from 400 nm to 1500 nm, commonly referred to as the visible and infrared spectral region. For the present invention, one preferred wavelength range is from 400 nm to 1500 nm. More preferably, the wavelength range is from 630 nm to 900 nm, and most preferably from 650 nm to 670 nm. A second preferred wavelength range is from 800 nm to 900 nm, preferably from 850 nm to 900 nm, and most preferably from 870 nm to 890 nm.

The result of the gas carry-under determination is then used as the basis of sending commands or command signals to wellsite pumps, pump controllers, or other devices, which would (1) regulate or control the rate of injecting additives into the different places such as the well itself wellbore(s), HP and other gas-oil separators, and other places of the processing equipment at the wellsite, and/or (2) provide other proper treatments including, but not limited to, varying the production rate, adjusting steam injection if there is any, adjusting the injection of chemicals for controlling corrosion etc, changing temperatures and combinations thereof. All these measures are intended to control gas carry-under.

The term "control gas carry-under" is used herein to mean defoam, antifoam, de-emulsify, or otherwise suppress gas entrainment in the formation fluid. In addition to using additives or chemicals to achieve these objectives, it is possible to use mechanical means or electromagnetic waves such as ultrasound waves or microwaves to force the separation of gas from formation fluid.

A number of additives are known to be effective for controlling gas carry-under for the purposes of the present invention. For instance, U.S. Pat. No. 5,853,617, issued to the same Assignee of the present invention, discloses a method and a composition for suppressing oil-based foams by using a combination of two conventional defoamers—a fluorosilicone and a non-fluorinated siloxane. Other suitable additive examples include conventional additives such as polydiorganosiloxanes, also known generically and generally as silicones. Polydialkylsiloxanes are preferred polydiorganosiloxanes. In particular, polydimethylsiloxanes (PDMS) are more preferred for the present invention to control gas carry-under. Fluorosilicones, partially fluorinated silicones, PDMS-polybutadiene block copolymers, silicone-glycol compounds, silicone-silica adducts, fatty acids, hydrolyzed lipids, combinations thereof and/or with PDMS or other polydiorganosiloxanes are other examples of additives suitable for the present invention. See U.S. Pat. No. 5,853,617. To the extent that U.S. Pat. No. 5,853,617 discloses various anti foaming and gas carry-under additive compositions, combinations, preparations, commercial sources, uses of these additives and the method of using these additives, the patent is incorporated herein by reference.

These gas carry-under-control additives may be used in a number of physical and/or chemical forms, such as pure (or undiluted) materials, solutions, emulsions, suspensions, blends, other type physical mixtures or admixtures, and combinations thereof. These additives may be pumped into the oil well premixed or separately, with or without any additional diluents or solvents. The same supply line or different supply lines may be used for different additives, depending on chemical and physical compatibilities, relative quantities required and other properties.

There are a number of ways the control of injections of additives may be accomplished. Depending on the number of wells at a particular site or offshore platform, the location of the controllers, the location of the operators and the degree of automation, there could be a plurality of controllers, both local and remote, a plurality of sample quills, a plurality of liquid measuring devices and a plurality of pumps, pump controllers, flow meters etc. The measurement signals, data, calculated results such as correlations and comparisons, command signals and feedback information or signals could be transmitted or communicated by wired or wireless means. Many functions can also be built into one unit, if preferred, to accord various benefits such as reducing the total number of controlling devices or units and increasing the speed of communications.

Another preferred embodiment of the present invention includes a transmission probe device using the principle of light scatter to determine when gas is present in the liquid stream. The more light scattered by a liquid sample passing through such a sensor, the higher the density of the liquid. Almost without exception, gas, either in dissolved or in the form of micro- or larger bubbles, can decrease the density of the liquid containing it. Therefor, a decrease in the density of a liquid exiting a separator indicates that the liquid includes entrained gas. This and any other sensor which can be used to measure a formation fluid liquid stream and produce a signal that can be used to determine the presence of entrained gas can be used with the system of the present invention.

While the foregoing disclosure is directed to a number of the preferred embodiments of the invention, various modifications will be apparent to and appreciated by those skilled in the art. Similarly, the theories and the examples are presented solely to illustrate details of the invention so one skilled in the art would more readily understand and appreciate the advantages.

What is claimed is:

1. A system for determining gas carry-under of formation fluid passing through at least one liquid and gas separator that provides a gas stream separated from a liquid formation fluid stream, comprising:

a sensor for providing sensor measurements of a parameter of interest relating to the liquid formation fluid stream that is indicative of the gas carry-under of the liquid formation fluid stream; and a processor utilizing the sensor measurements for determining a degree of the gas carry-under of the liquid formation fluid stream, wherein the sensor is a densitometer, a transmission probe providing measurements corresponding to the optical density of the liquid formation fluid stream, or an attenuated total reflectance probe providing absorbance spectra corresponding to the gas content of the liquid formation fluid stream.

2. The system of claim 1, wherein the sensor is an attenuated total reflectance probe providing absorbance spectra corresponding to the gas content of the liquid formation fluid stream further comprising a photometer.

3. The system of claim 2 wherein the absorbance spectra are made at a wavelength ranging from 400 nm to 1500 nm.

4. The system of claim 1, wherein the processor displays the degree of gas carry-under on an onsite display.

5. The system of claim 1 further comprising a chemical injection unit for supplying a chemical to the formation fluid for controlling gas carry-under of the formation fluid.

6. The system of claim 5, the chemical injection unit comprising:

a source of at least one chemical for injection into the formation fluid at a selected location thereof for at least inhibiting foam formation of foam in the formation fluid; and a chemical supply device for supplying the chemical to the selected location.

7. The system of claim 6, wherein the processor controls the operation of the chemical injection unit to increase the amount of chemical supplied to the formation fluid when the degree of gas carry-under is outside a predefined limit.

8. The system of claim 1, wherein the processor is located at one of (i) a site of the at least one separator; and (ii) a remote location.

9. The system of claim 7, wherein the chemical injection unit injects the at least one chemical at a location selected from a group consisting of (i) in the at least one separator; (ii) in a well producing the formation fluid; (iii) at a wellhead at the surface; and (iv) in a selected number of wells from a plurality of wells providing formation fluid to the at least one separator.

10. A method of controlling gas carry-under of formation fluid passing through at least one liquid and gas separator that provides a gas stream separated from a liquid formation fluid stream, the method comprising treating the production fluid using a system comprising:

a sensor for providing sensor measurements of a parameter of interest relating to the liquid formation fluid stream that is indicative of the gas carry-under of the liquid formation fluid stream; and a processor utilizing the sensor measurements for determining a decree of the gas carry-under of the liquid formation fluid stream, wherein the sensor is a densitometer, a transmission probe providing measurements corresponding to the optical density of the liquid formation fluid stream, or an attenuated total reflectance probe providing absorbance spectra corresponding to the gas content of the liquid formation fluid stream.

11. The method of claim 10 wherein the system further comprises a chemical injection unit for supplying a chemical to the formation fluid for controlling gas carry-under of the formation fluid.

12. The method of claim 11 wherein the chemical injection unit comprises:

a source of at least one chemical for injection into the formation fluid at a selected location thereof for at least inhibiting foam formation of foam in the formation fluid; and a chemical supply device for supplying the chemical to the selected location.

13. The method of claim 12 wherein the processor controls the operation of the chemical injection unit to increase the amount of chemical supplied to the formation fluid when the degree of gas carry-under is outside a predefined limit.

* * * * *